United States Patent
Scheker

(10) Patent No.: US 8,641,770 B2
(45) Date of Patent: Feb. 4, 2014

(54) PROSTHESIS FOR THE BASAL JOINT OF THE THUMB

(75) Inventor: Luis Roman Scheker, Glenview, KY (US)

(73) Assignee: Aptis Medical, LLC, Glenview, KY (US)

( * ) Notice: Subject to any disclaimer, the term of this patent is extended or adjusted under 35 U.S.C. 154(b) by 107 days.

(21) Appl. No.: 13/358,550

(22) Filed: Jan. 26, 2012

(65) Prior Publication Data
US 2013/0197655 A1 Aug. 1, 2013

(51) Int. Cl.
*A61F 2/42* (2006.01)

(52) U.S. Cl.
USPC ...................................... 623/21.16

(58) Field of Classification Search
USPC .......................... 623/21.15–21.17
See application file for complete search history.

(56) References Cited

U.S. PATENT DOCUMENTS

| | | | |
|---|---|---|---|
| 4,304,011 A * | 12/1981 | Whelan, III | ............... 623/21.16 |
| 4,653,489 A | 3/1987 | Tronzo | |
| 4,955,916 A | 9/1990 | Carignan | |
| 5,192,282 A | 3/1993 | Draenert | |
| 5,702,469 A | 12/1997 | Whipple et al. | |
| 5,702,471 A | 12/1997 | Grundei et al. | |
| 5,888,204 A | 3/1999 | Ralph | |
| 6,126,690 A | 10/2000 | Ateshian | |
| 6,554,830 B1 | 4/2003 | Chappius | |
| 6,565,572 B2 | 5/2003 | Chappius | |
| 6,755,835 B2 | 6/2004 | Schultheiss et al. | |
| 6,811,568 B2 | 11/2004 | Minamikawa | |
| 7,354,442 B2 | 4/2008 | Sasso et al. | |
| 7,608,097 B2 | 10/2009 | Kyle | |
| 7,717,947 B1 | 5/2010 | Wilberg et al. | |
| 8,292,966 B2 * | 10/2012 | Morton | ...................... 623/21.19 |
| 2005/0010303 A1 | 1/2005 | Nogier | |
| 2009/0254190 A1 | 10/2009 | Gannoe | |
| 2010/0010636 A1 | 1/2010 | Shultz | |
| 2010/0030135 A1 | 2/2010 | Mitchell | |
| 2011/0060373 A1 | 3/2011 | Russell et al. | |
| 2011/0112652 A1 | 5/2011 | Hansson | |

FOREIGN PATENT DOCUMENTS

JP 10211213 8/1998

OTHER PUBLICATIONS

'De La Caffiniere Arthroplasty for Basal Thumb Joint Osteoarthritis', by R.M. Nicholas and J.W. Calderwood. British Editorial Society of Bone and Joint Surgery, c1992.
'Total Joint Arthroplasty for the Arthritic Thumb Carpometacarpal Joint' by Alejandro Badia, Chief of Hand Surgery, Baptist Hospital of Miami, FL, Quadrant HealthCom Inc.c2008.

* cited by examiner

*Primary Examiner* — David Isabella
*Assistant Examiner* — Ann Schillinger
(74) *Attorney, Agent, or Firm* — Camoriano and Associates; Theresa Camoriano; Guillermo Camoriano

(57) ABSTRACT

A basal joint of the thumb prosthesis includes a socket element to be secured to the trapezoid and capitate, and a metacarpal component to be secured to the first metacarpal. A ball on the metacarpal component is received and substantially enclosed by the socket element.

12 Claims, 10 Drawing Sheets

PROSTHESIS FOR THE BASAL JOINT OF THE THUMB

BACKGROUND

The present invention relates to a prosthesis for the basal joint of the thumb.

Due to a number of factors, including age and wear, the joint between the trapezium bone of the wrist and the first metacarpal (the bone at the proximal end of the thumb) often degenerates, resulting in carpo-metacarpal arthritis. Additionally, STT (scaphoid, trapezium, trapezoid) arthritis may result at the proximal end of the trapezium. These conditions may necessitate inserting a prosthesis for the basal joint of the thumb.

Prior art prostheses, such as that disclosed by Whipple U.S. Pat. No. 5,702,469, have attempted to resolve the carpo-metacarpal arthritis problem by providing a ball and socket arrangement (See FIG. 2 of Whipple '469) wherein the metacarpal component includes a rod S1 driven into the first metacarpal, with the ball portion projecting proximally from the first metacarpal, and the trapezium component having a rod S2 driven into the trapezium, with a concave surface projecting distally from the trapezium. This concave surface receives the ball of the metacarpal component for limited rotational support of the first metacarpal on the trapezium. This prior art design relies on a ligament between the first and second metacarpals to provide support and prevent dislocation of the first metacarpal from the trapezium.

In Whipple and other prior art designs, the installation is hindered by the need to save the ligament between the first and second metacarpals in order to have this ligament provide the necessary support to prevent the dislocation of the ball from its socket. This, combined with the usage of the existing trapezium to anchor the trapezium component, results in very limited accessibility for installation of a ball and socket arrangement. The result is a ball which can easily be dislocated from the member that supports it, which causes failure of the prosthesis.

SUMMARY

The present invention provides a prosthesis for the basal joint of the thumb. In a preferred embodiment, the prosthesis replaces the trapezium with a socket that substantially encloses the ball (the first metacarpal component) to eliminate the possibility of the ball dislocating from the prosthesis. The member that defines the socket has a flat side that abuts the side of the trapezoid bone and is secured to the trapezoid bone by means of screws that extend through the member and into the side of the trapezoid bone. The trapezoid bone is itself supported on the scaphoid bone, so the socket is also supported by the scaphoid via the trapezoid. The first metacarpal component is secured to the first metacarpal bone by a stem that extends into a pre-cut recess in the first metacarpal bone and by a plate that abuts and conforms to the outer surface of the first metacarpal bone and that has holes that receive screws that extend through the plate and into the first metacarpal bone. This arrangement provides for good securement of the prosthesis in cortical bone and good support of the prosthesis so it does not become displaced from the respective bones and so the ball of the prosthesis does not become displaced from the socket of the prosthesis.

DESCRIPTION

Figure 1:
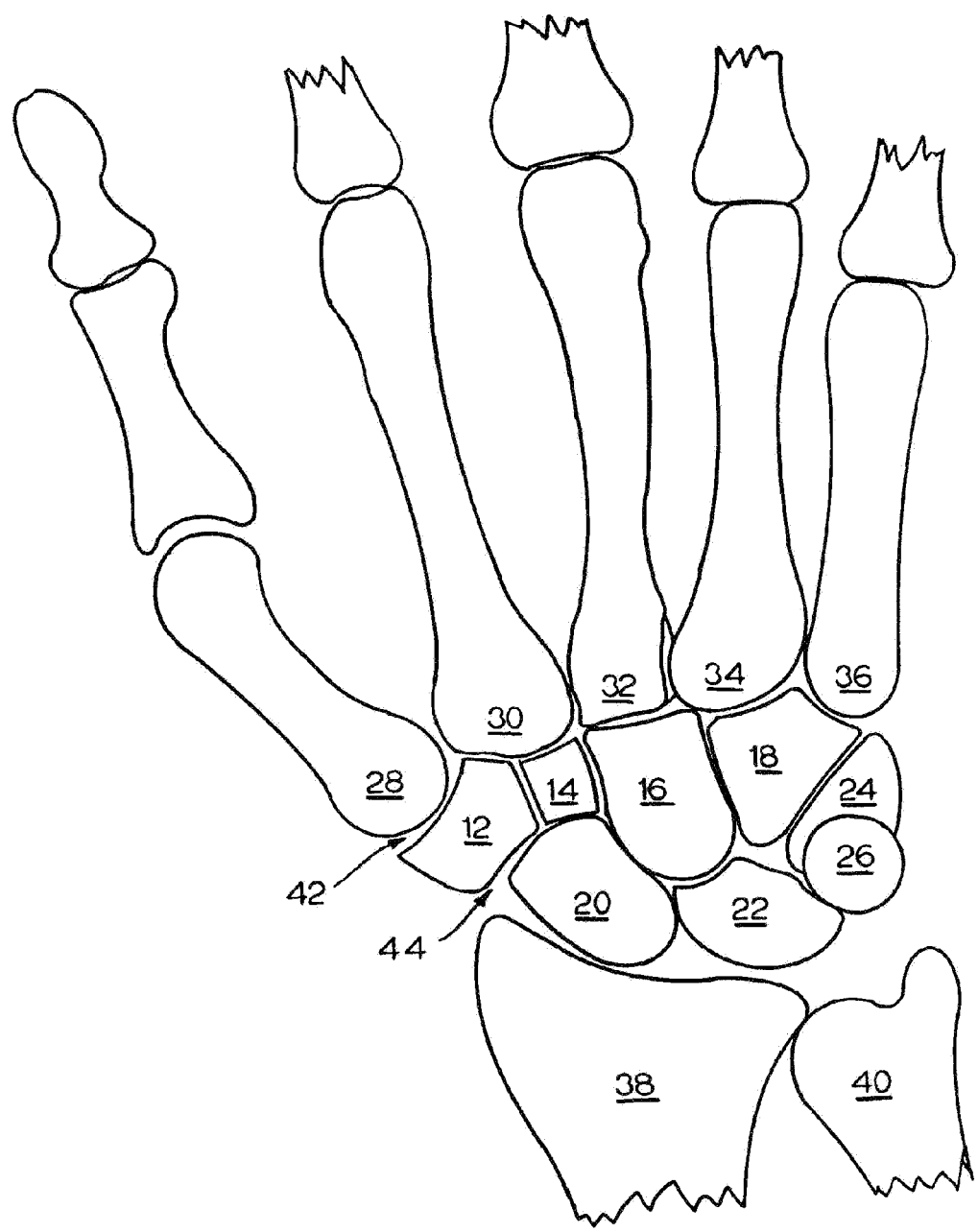
FIG. 1 is a partially broken-away, anterior skeletal view of the human wrist, and shows the base of the fingers and thumb.

FIG. 1 is a skeletal schematic of the carpal and metacarpal bones of the human wrist 10. These bones include the trapezium 12, the trapezoid 14, the capitate 16, the hamate 18, the scaphoid 20, the lunate 22, the triquetrum 24, the pisiform 26, the first metacarpal 28 (which is the first or proximal bone of the thumb), the second metacarpal 30, the third metacarpal 32, the fourth metacarpal 34, and the fifth metacarpal 36. Also shown are the radius 38 and the ulna 40 bones of the arm.

As indicated earlier, the joint 42 between the trapezium 12 and the first metacarpal 28 (the bone at the proximal end of the thumb) often degenerates, resulting in carpo-metacarpal arthritis. Additionally, STT (scaphoid, trapezium, trapezoid) arthritis may result at the proximal end 44 of the trapezium. These conditions may be treated by providing a prosthesis for the basal joint of the thumb.

Figure 2:
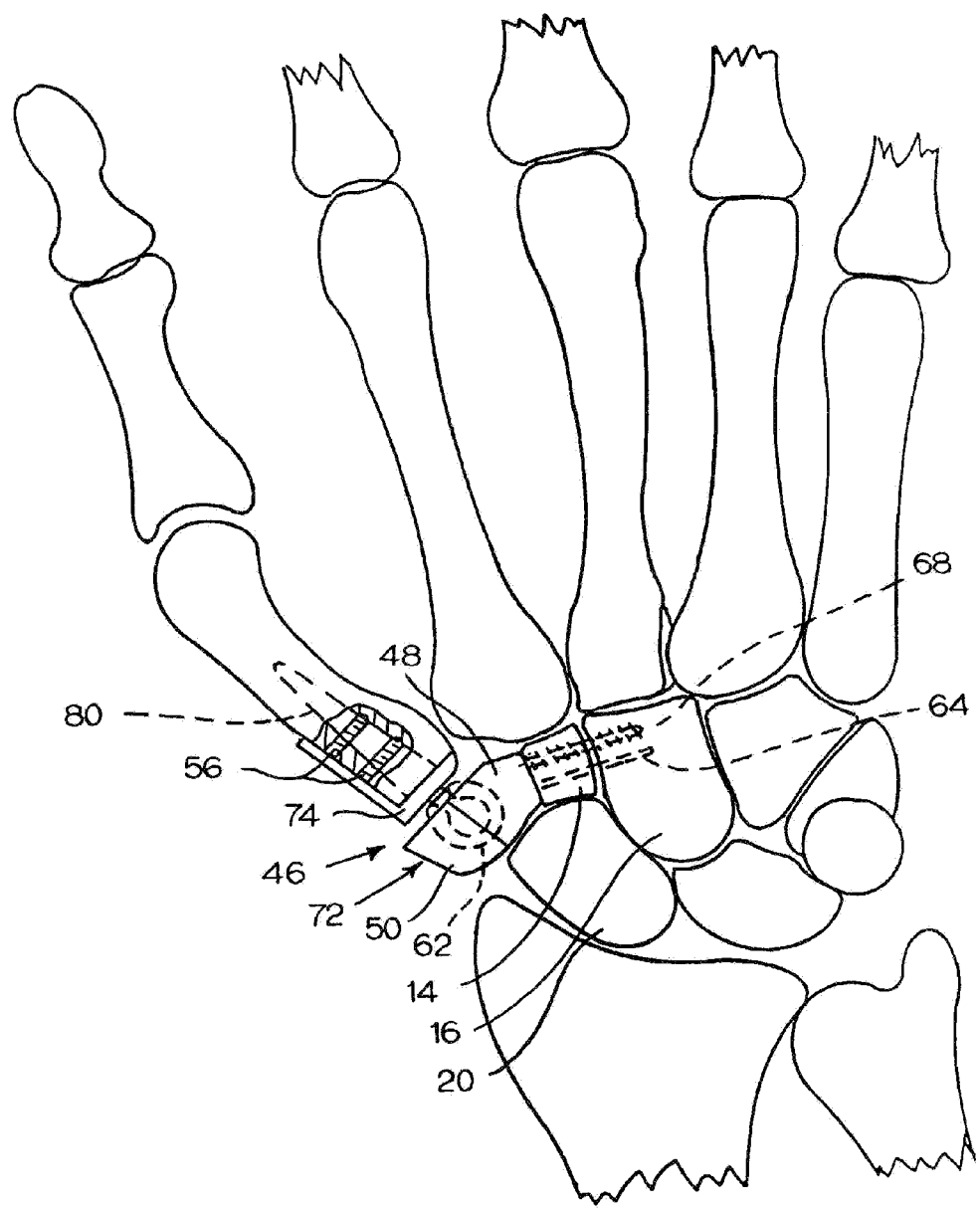
FIG. 2 is a view similar to FIG. 1A, but with a prosthesis of the basal joint of the thumb shown partially in section.
Figure 3:
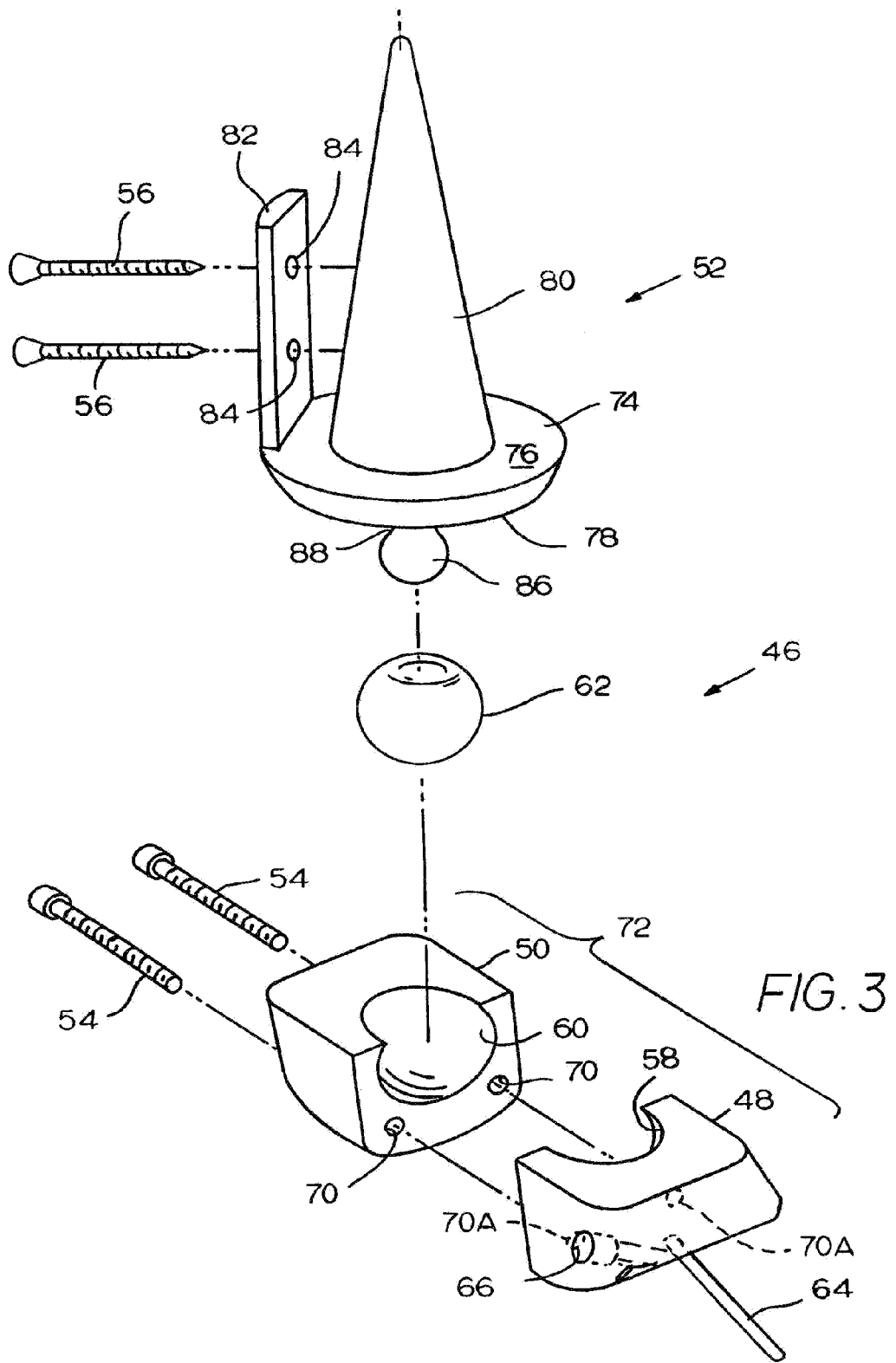
FIG. 3 is an exploded, perspective view of the prosthesis of FIG. 2.
Figure 4:
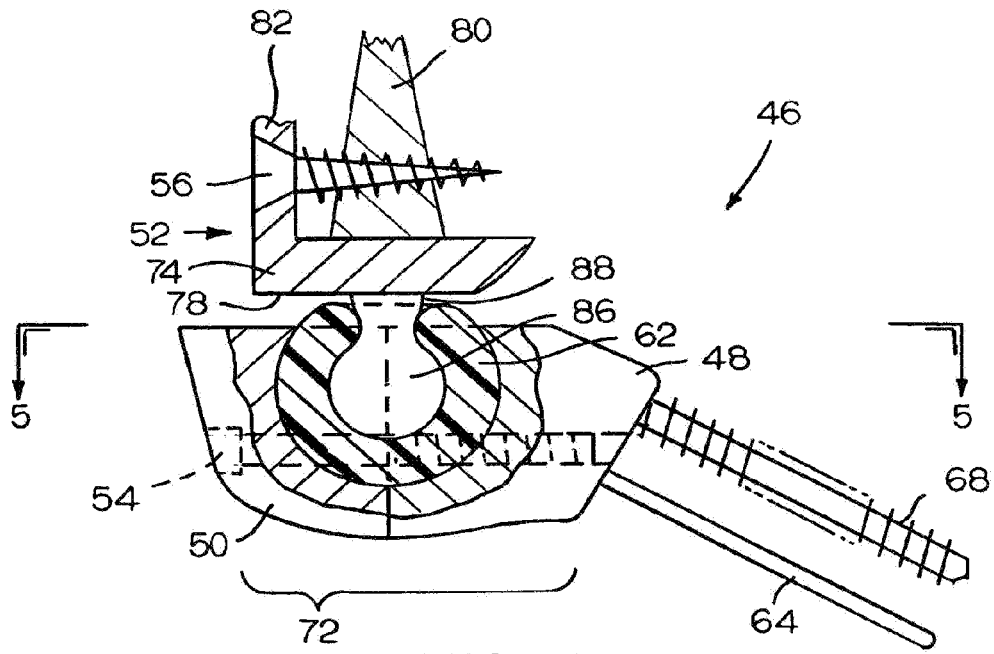
FIG. 4 is a broken away view, partially in section, of the prosthesis of FIGS. 2 and 3.
Figure 5:
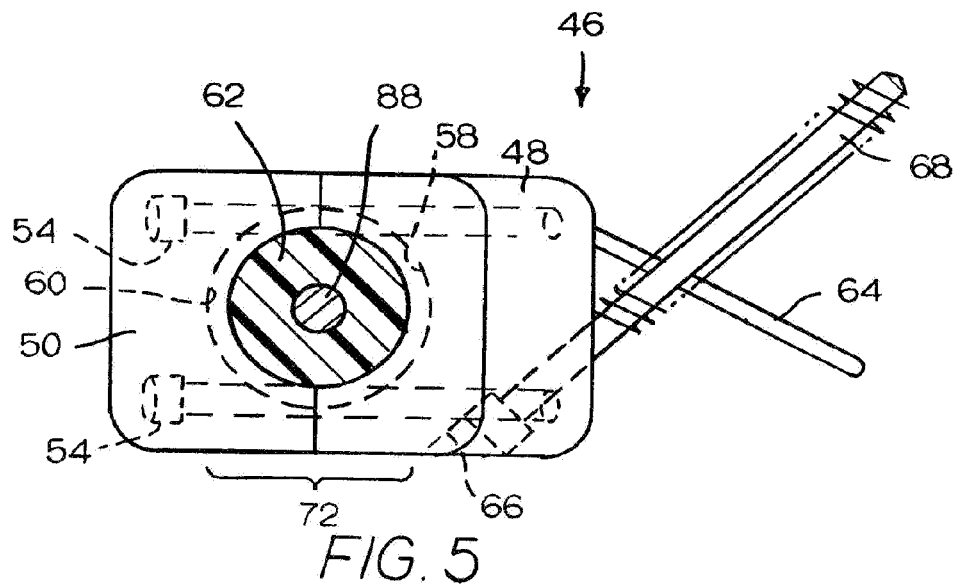
FIG. 5 is a section view along line 5-5 of FIG. 4.

FIG. 2 shows a prosthesis for the basal joint of the thumb 46 made in accordance with one embodiment of the present invention and installed on the human hand. FIGS. 3, 4, and 5 show this prosthesis 46 in more detail. The prosthesis 46 includes a socket base 48, a socket cap 50, and a first metacarpal component 52. There are screws 54 which secure the socket cap 50 to the socket base 48, and screws 56 which secure the metacarpal component 52 to the first metacarpal bone 28.

The socket base 48 is a substantially rectangular member which defines an open, partial spherical recess 58 which cooperates with a similar partial spherical recess 60 on the socket cap 50 to define a spherical socket cavity that receives and captures the ball 62 of the metacarpal component 52 when the socket cap 50 and socket base 48 are secured together, as discussed in more detail later.

The socket base 48 also includes a rod 64 which is fixed to the socket base 48 and projects outwardly from the side opposite the partial-spherical cavity 58. This rod 64 is inserted into a bore drilled through the trapezoid 14 and, if desired, into the capitate 16 to help support the prosthesis 46 on these carpal bones 14, 16. A through opening 66 extends crosswise through the socket base 48 (See FIGS. 3 and 5) to receive a screw 68 which secures the socket base 48 to the trapezoid 14 and the capitate 16, as shown in FIG. 2. The opening 66 is larger at the head portion of the screw 68 than along the shank portion of the screw, so the screw 68 is retained on the socket base 48. It can be seen in FIGS. 4 and 5 that the rod 64 and screw 68 are angled in different directions so they cross and then diverge from each other. This helps ensure that they remain anchored in the bones into which they extend.

The socket cap 50 is practically a mirror image of the socket base 48, except it does not have the rod 64 or the crosswise opening 66. Two parallel through openings 70 in the socket cap are aligned with corresponding threaded bores 70A in the socket base 48 so that the screws 54 can extend through the socket cap 50 and can be threaded into the socket base 48 to secure the socket cap 50 to the socket base 48 and form a socket assembly 72 as shown in FIGS. 4 and 5. Again, the head end of the openings 70 have a larger diameter than the remainder of the openings 70 in order to retain the screws 54.

As best appreciated in FIG. 4, the socket assembly 72 forms a partial spherical socket that substantially encloses and traps the inner ball 86 and outer ball 62 of the metacarpal component 52 so that it is not possible to dislodge the inner and outer balls 86, 62 from the socket assembly 72 without first separating the socket cap 50 from the socket base 48, as long as the inner and outer balls 86, 62 and the socket assembly 72 remain intact.

In the embodiment shown, the socket assembly 72 defines a socket that is approximately 75% of a sphere, and the balls 86, 62 define approximately 75% of a sphere, with a stem 88 projecting away from the ball 86, away from the socket, and into the first metacarpal bone 28. By forming 75% of a spherically-shaped socket which encloses 75% of a spherical ball, the socket assembly 72 is said to enclose the ball 75%. It is preferred that the socket assembly 72 enclose the ball 86 at least 60% and most preferable that the socket assembly 72 enclose the ball 86 at least 70% in order to ensure that the ball 86 will not be accidentally displaced from the socket assembly 72, while still permitting free rotation of the ball 86 relative to the socket assembly 72.

Referring again to FIG. 3, the metacarpal component 52 includes a substantially flat circular plate 74 defining an upper surface 76 and a lower surface 78. A tapered stem 80 (conically shaped) extends upwardly from the middle of the upper surface 76 of the plate 74, tapering from a larger diameter at the upper surface 76 (the proximal end of the tapered peg 80) to a smaller diameter at the distal end of the tapered peg 80.

A securement plate 82 projects upwardly from the outer edge of the circular plate 74. The surface of the securement plate 82 adjacent to the stem 80 conforms to the shape of the outer surface of the first metacarpal bone 28, so the metacarpal component 52 wraps around from the bottom of the bone 28 to the side of the bone, as well as having a stem 80 that extends to the interior of the bone.

Figure 7:
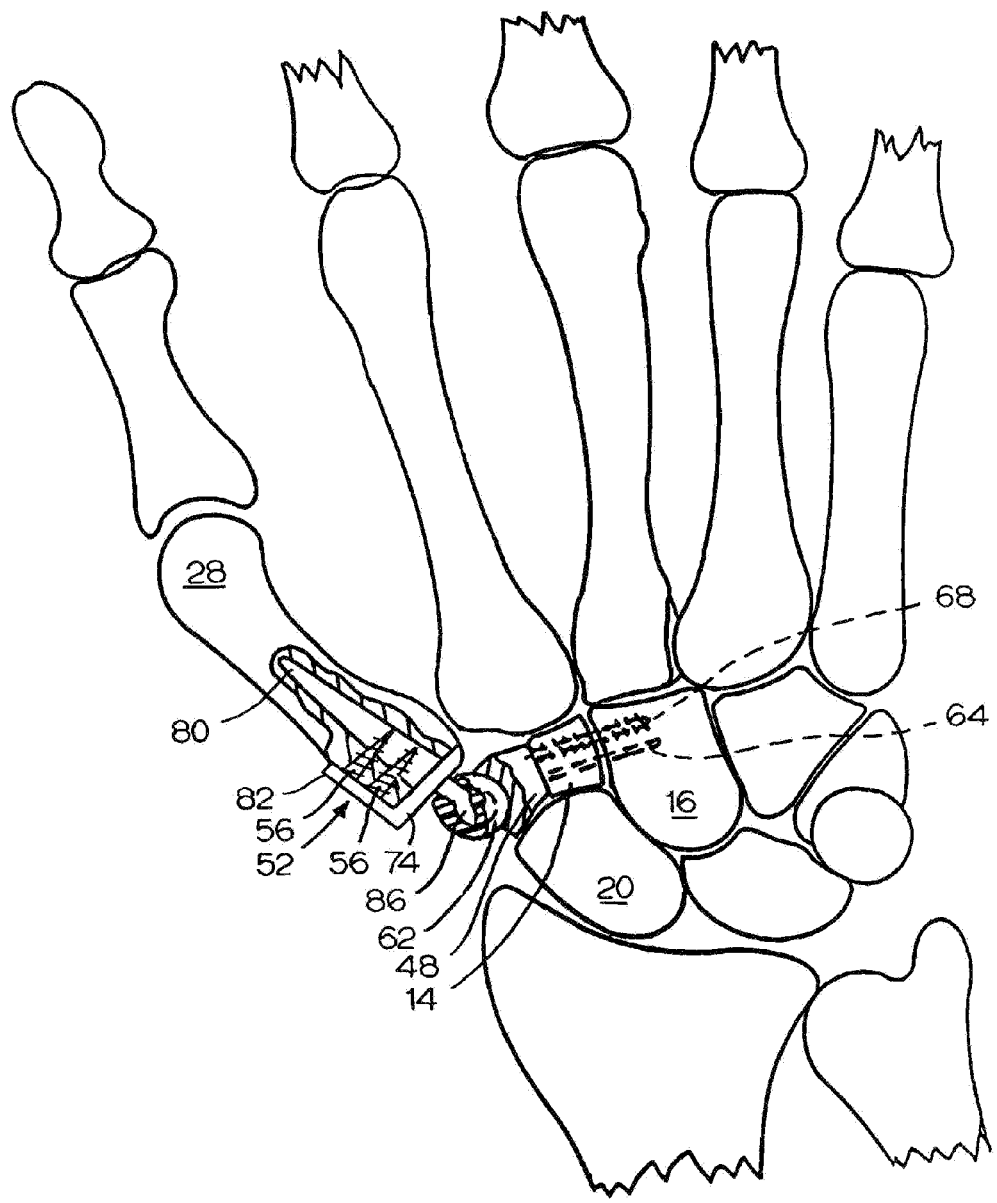
FIG. 7 is a view similar to FIG. 6, but with the second part of the first element installed and shown partially broken away and in section, and with the second element of the prosthesis of FIG. 3 installed.

The securement plate 82 defines through openings 84 through which screws 56 extend to secure the metacarpal component 52 to the first metacarpal 28, as shown in FIGS. 2 and 7. In this embodiment, the screws 56 extend through the securement plate 82, into the first metacarpal 28, and into the tapered stem 80, to ensure a secure attachment of the metacarpal component 52 onto the first metacarpal 28, as discussed in more detail later.

Referring now to FIG. 4, a small ball 86 projects downwardly from, and is connected to, the bottom surface 78 of the circular plate 74 via a neck 88, the arrangement resembling a small, upside down, trailer hitch ball. The plate 74, neck 88, and ball 86 preferably are made of metal. There is an additional hollow outer ball 62 which snaps over the smaller ball 86. This can be designed to be a very tight fit as the outer ball 62 is not expected to rotate or have any movement relative to the smaller ball 86. In a preferred embodiment, most of the components of the prosthesis 46 are made from an acceptable medical grade metal such as a medical grade stainless steel alloy or titanium. The outer ball 62 is made from an inert plastic, such as Teflon or some other self-lubricating plastic, to provide a non-galling joint between the outer ball 62 and the partial spherical cavity formed by the two cavities 58, 60 of the socket base 48 and socket cap 50 respectively.

Since the outer ball 62 is assembled onto the metacarpal component 52 before the metacarpal component 52 is installed in the first metacarpal bone 28, the outer ball 62 may be press-fit onto the inner ball 86 using any amount of force required to accomplish the goal. Should the outer ball 62 become worn with use, a follow-up surgery may be undertaken to remove and replace the outer ball 62 by unscrewing the socket cap 50 from the socket base 48 and cutting the ball 62 out of the metacarpal component 52. A new replacement outer ball 62 may then be placed over the smaller inner ball 86.

The new outer ball 62 need not be a one piece ball. For instance, a two piece outer ball may be used to fit snugly around the smaller ball 86. Since the socket assembly 72 substantially encloses the outer ball 62, a two-piece outer ball design will be held securely in place by the socket assembly 72. A two-piece outer ball could simply be the same as the outer ball 62 but cut in half along the vertical axis shown in FIG. 4.

Figure 1A:
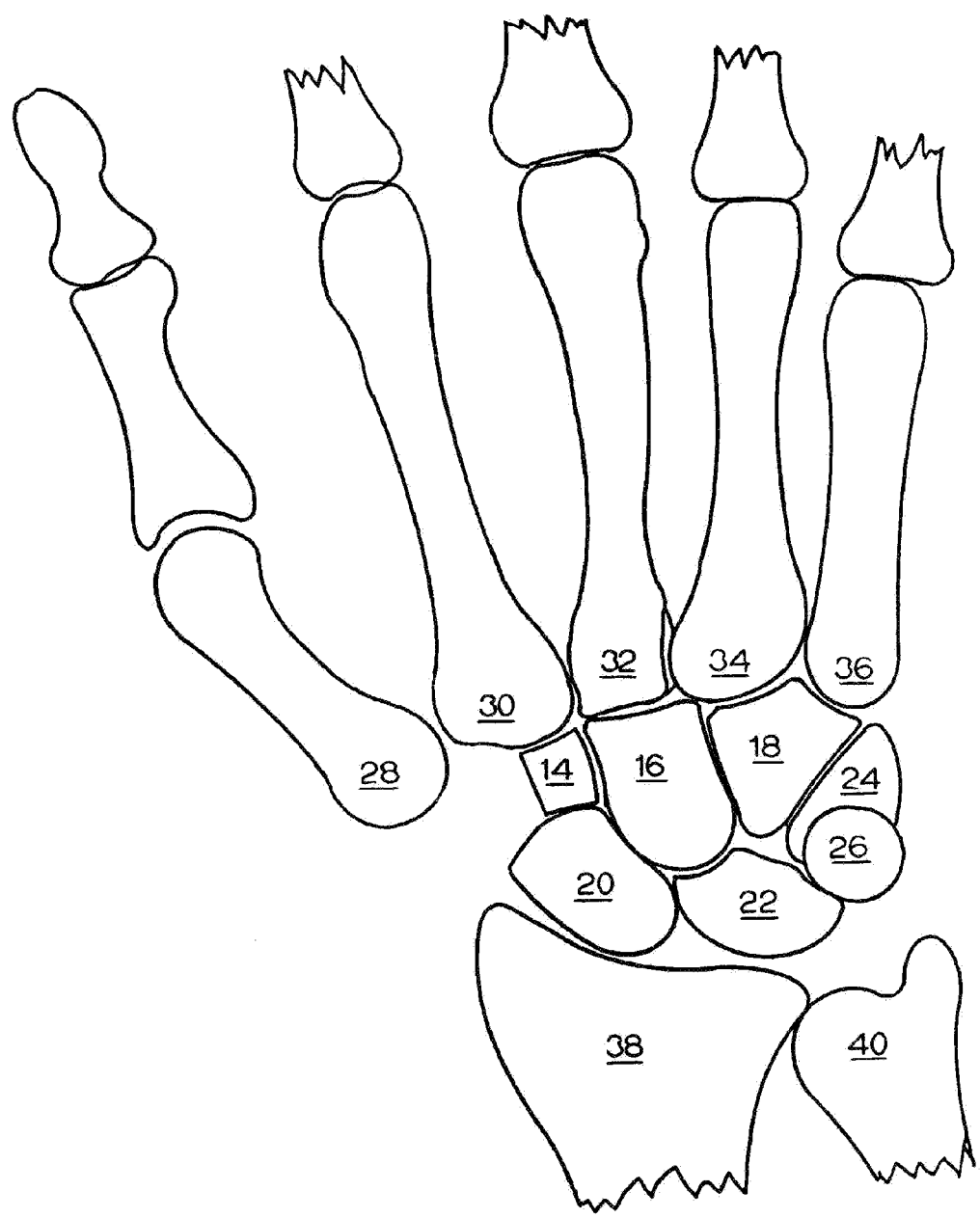
FIG. 1A is a view similar to FIG. 1, but with the trapezium bone excised.

A typical installation of the prosthesis 46 begins with excising the trapezium 12. FIG. 1 shows the trapezium 12 in place, and FIG. 1A shows the hand after the trapezium 12 has been excised.

Figure 6:
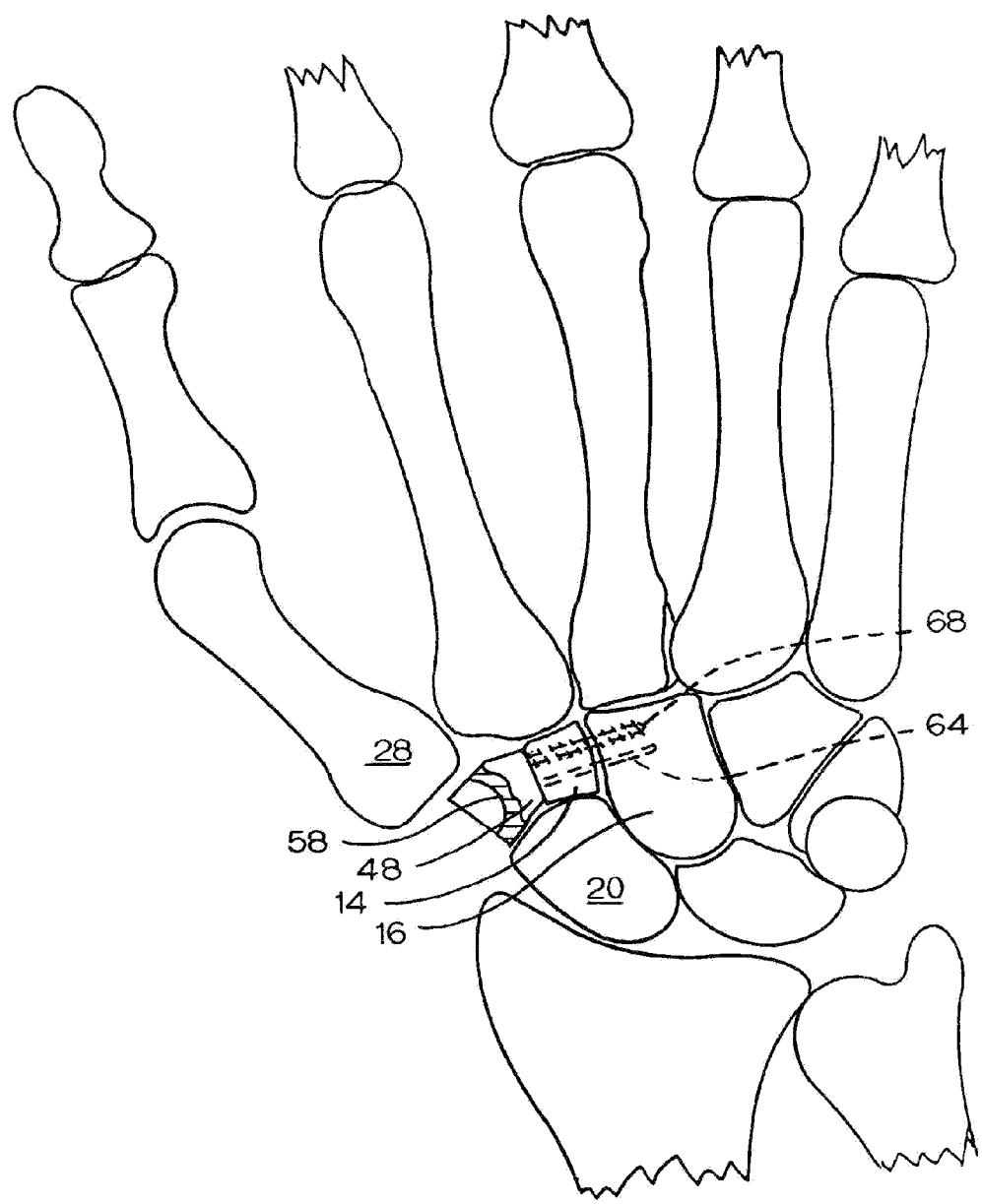
FIG. 6 is a view similar to FIG. 1A, but with the part of the first element of the prosthesis of FIG. 3 installed and shown partially broken away and in section.

Next, the socket base 48 (See FIG. 6) is mounted to the trapezoid 14 and capitate 16 bones via the rod 64 and the screw 68. Two holes are drilled into the trapezoid and capitate; the first hole receives the rod 64 projecting from the socket base 48, and then the screw 68 is screwed into the second hole. By extending completely through the trapezoid bone 14 and into the capitate bone 16, the rod 64 and screw 68 are supported by three layers of hard, cortical bone material.

Referring now to FIG. 7, after a small portion of the proximal end of the first metacarpal 28 has been excised to accommodate the circular plate 74 and the securement plate 82 of the metacarpal component 52, a tapered bore is drilled up into the first metacarpal 28 to receive the tapered peg 80 of the metacarpal component 52. The tapered peg 80 is then inserted into the bore until the circular plate 74 abuts the bottom of the first metacarpal bone 28. Then screws 56 are inserted through the openings 84 in the securement plate 82 to secure the metacarpal component 52 to the first metacarpal 28. The screws 56 extend into the first metacarpal 28 and into the tapered peg 80.

Figure 8:
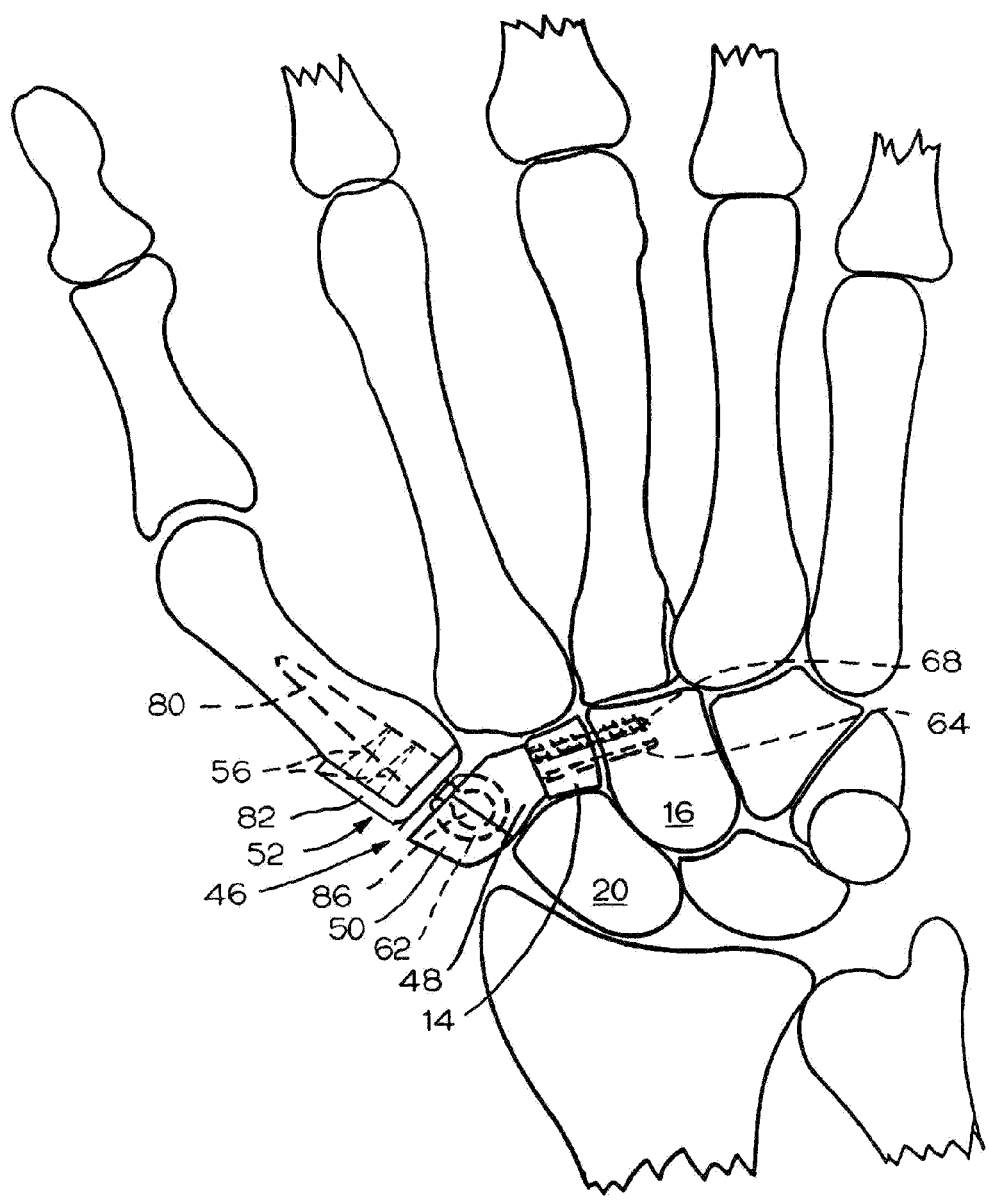
FIG. 8 is a view similar to FIG. 7, but with none of the elements broken away or in section.

Finally, referring to FIG. 8, the socket cap 50 is installed over the ball 62 of the metacarpal component 52 to substantially enclose and trap the outer ball 62 and the inner ball 86. The socket cap 50 is secured to the socket base 48 via the screws 54, shown in FIGS. 3 and 4.

It may be appreciated that the first metacarpal bone 28 is thus supported for rotation by the ball 62 trapped inside the socket assembly 72. Since the ball 62 is entrapped by the socket assembly 72, the first metacarpal component 52 will not disengage from the socket assembly 72 and will continue to be supported, even if there are no ligaments supporting it.

The socket assembly 72 is in turn supported by the trapezoid 14 and the capitate 16 via the rod 64 and the screw 68, with the side of the socket base 48 having a large surface area abutting the side of the trapezoid 14. Finally, since the trapezoid 14, and to a lesser extent the capitate 16, are supported by the scaphoid 20, the prosthesis 46 is also supported by the scaphoid 20. Therefore the thumb, which was originally supported by the trapezium which in turn was supported by the scaphoid, is now supported by the socket assembly 72 of the prosthesis 46 which, in turn, is supported by the scaphoid 20 via the trapezoid 14 and the capitate 16.

In this manner, the prosthesis 46 provides its own secure mounting arrangement for the metacarpal component 52, and does not rely on ligaments between the first metacarpal 28 and the second metacarpal 30 to prevent the dislocation of the first metacarpal 28 from the prosthesis, as in the prior art.

Figure 9:
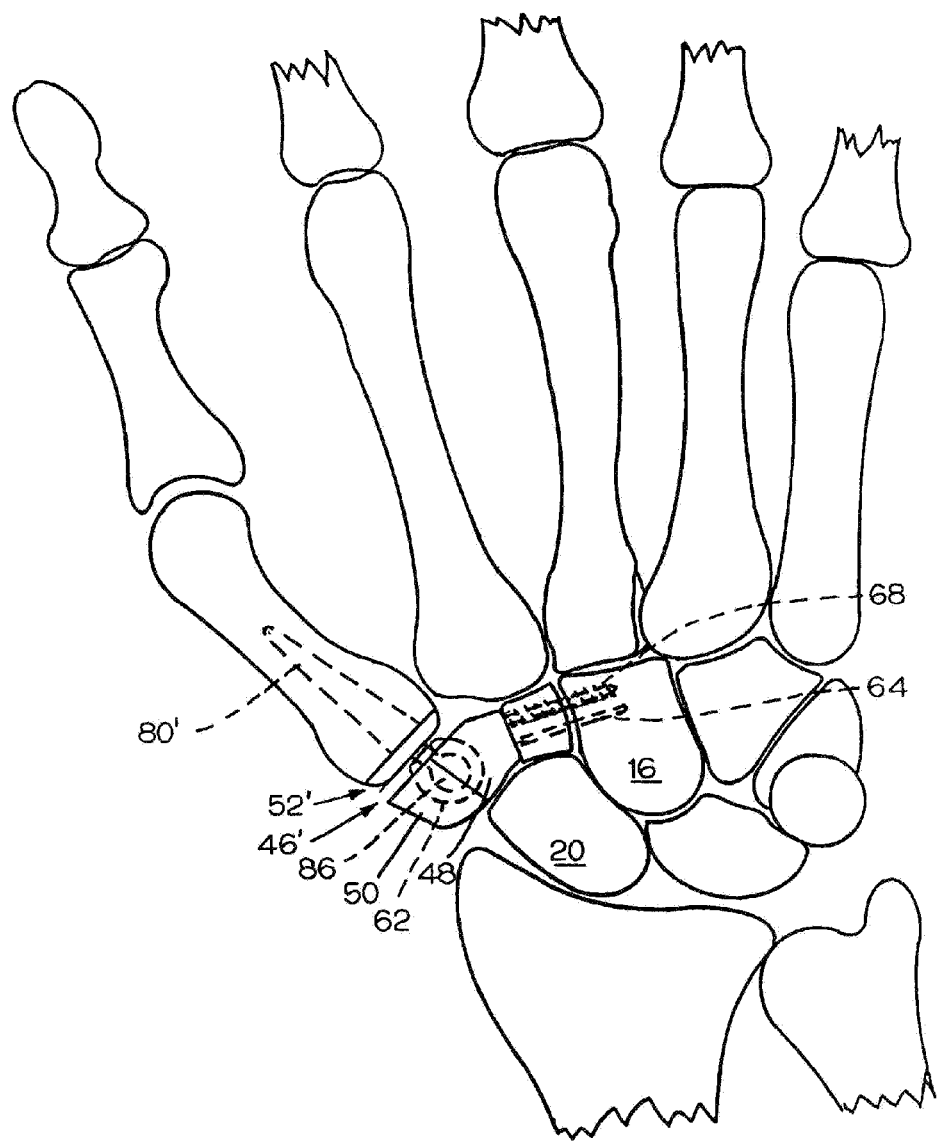
FIG. 9 is a view similar to FIG. 8, but for a second embodiment of the prosthesis.

FIG. 9 shows a second embodiment of a prosthesis 46'. This embodiment 46' is similar to the embodiment 46 described earlier. The only difference is that the metacarpal component 52' does not have the securement plate 82 and the screws 56 to secure the metacarpal component 52' to the first metacarpal 28. Instead, it relies on the tapered peg 80', which is cemented into a bore drilled up into the first metacarpal 28, to hold the metacarpal component 52 in place. All other components are identical, and this metacarpal component 52' operates in the same manner as the metacarpal component 52 described above.

Figure 10:
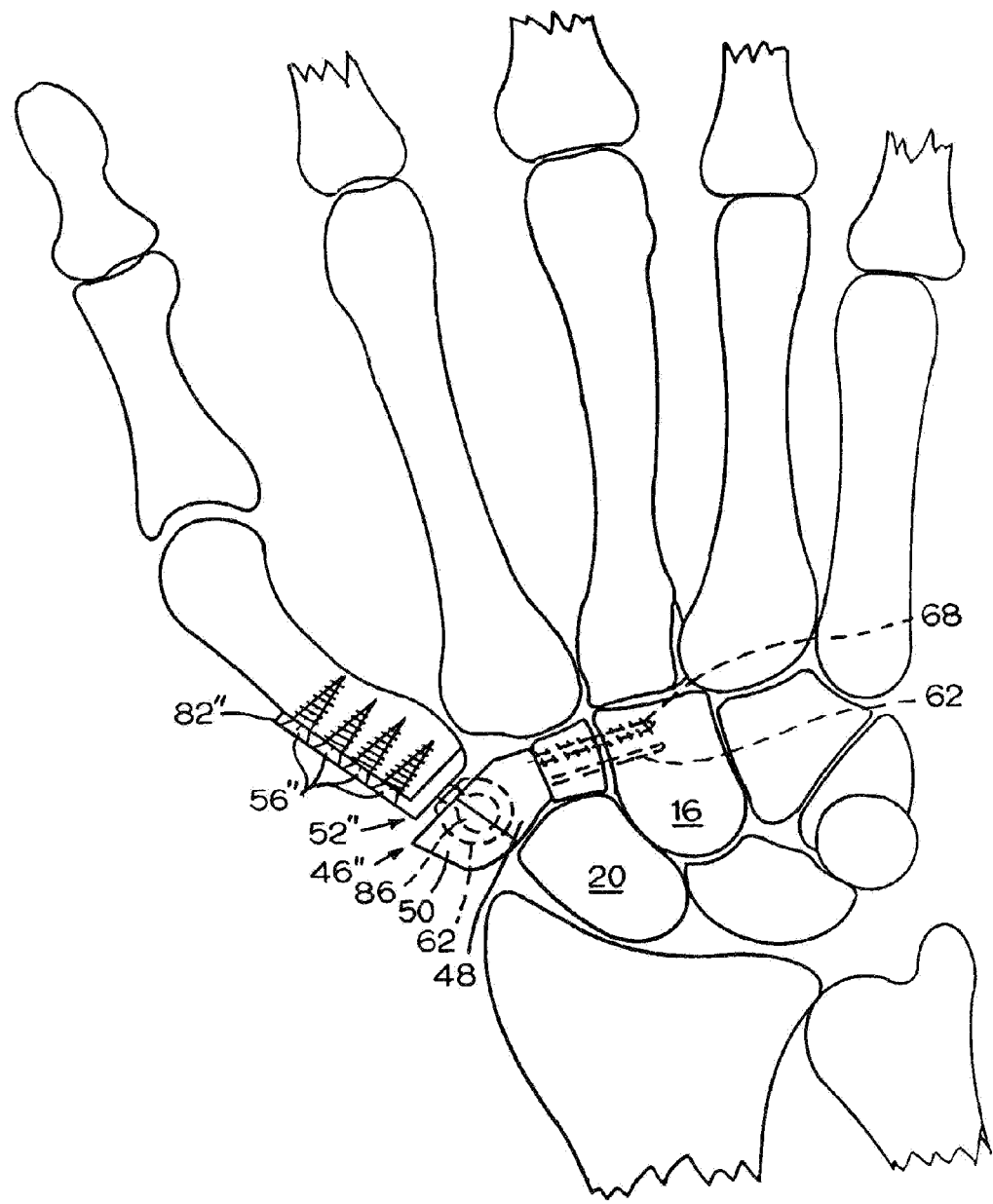
FIG. 10 is a view similar to FIG. 7, but for a third embodiment of the prosthesis.

FIG. 10 shows a third embodiment of a prosthesis 46". This embodiment 46" is similar to the embodiment 46 described earlier. The only difference is that the metacarpal component 52" does not have the tapered peg 80. Instead, it relies on an extended securement plate 82" and a plurality of screws 56" that secure the securement plate 82" to the first metacarpal 28. All other components are identical, and this metacarpal component 52' operates in the same manner as the metacarpal component 52 described above.

While the embodiments described above show several arrangements for a prosthesis for the basal joint of the thumb, it will be obvious to those skilled in the art that modifications could be made to these arrangements without departing from the scope of the present invention as claimed.

What is claimed is:

1. A prosthesis for the basal joint of the thumb, comprising:
   a socket member including a socket base portion and a socket cap portion, each of said socket base portion and socket cap portion defining a partial spherical recess; and means for securing said socket base portion and socket cap portion together so that said partial spherical recesses cooperate to form an internal, partial spherical socket;
   a first metacarpal component including means for securing the first metacarpal component at the proximal end of a first metacarpal bone and including a proximally extending, partial spherical projection, said partial spherical projection being received and supported for rotation by said partial spherical socket, with the partial spherical socket enclosing the partial spherical projection sufficiently that the partial spherical projection is entrapped by and cannot be dislodged from the partial spherical socket as long as the partial spherical projection remains intact and the socket base portion and socket cap portion are secured together and remain intact.

2. A prosthesis for the basal joint of the thumb as recited in claim 1, wherein said partial spherical projection is at least 70% enclosed by said partial spherical socket.

3. A prosthesis for the basal joint of the thumb as recited in claim 2, wherein said socket member has an external size and shape that is substantially similar to the human trapezium when the socket base and socket cap are secured together.

4. A prosthesis for the basal joint of the thumb as recited in claim 3, wherein said means for securing the first metacarpal component at the proximal end of a first metacarpal bone includes a tapered stem sized and shaped to be received in a longitudinal bore in a first metacarpal bone.

5. A prosthesis for the basal joint of the thumb as recited in claim 3, wherein said socket base portion has a first side shaped to conform to the side of the trapezoid bone, said socket base portion defining an internally threaded opening extending to the first side for receiving a screw to secure the socket base portion to the trapezoid.

6. A prosthesis for the basal joint of the thumb as recited in claim 1, wherein said socket member has an external size and shape that is substantially similar to the human trapezium when the socket base and socket cap are secured together.

7. A prosthesis for the basal joint of the thumb as recited in claim 1, wherein said means for securing the first metacarpal component at the proximal end of a first metacarpal bone includes a securement plate having a surface that conforms to the shape of the outer surface of a first metacarpal bone, said securement plate defining at least one opening; and at least one screw having a shank sized to extend through said opening and a head sized to be retained by said opening.

8. A prosthesis for the basal joint of the thumb, comprising:
   a socket member including a socket base portion and a socket cap portion, each of said socket base portion and socket cap portion defining a partial spherical recess; and means for securing said socket base portion and socket cap portion together so that said partial spherical recesses cooperate to form an internal, partial spherical socket;
   a first metacarpal component including means for securing the first metacarpal component at the proximal end of a first metacarpal bone and including a proximally extending, partial spherical projection, said partial spherical projection being received and supported for rotation by said partial spherical socket, with the partial spherical socket enclosing the partial spherical projection sufficiently that the partial spherical projection is retained in the partial spherical socket as long as the partial spherical projection remains intact and the socket base portion and socket cap portion are secured together and remain intact;
   wherein said means for securing the first metacarpal component at the proximal end of a first metacarpal bone includes a securement plate having a surface that conforms to the shape of the outer surface of a first metacarpal bone, said securement plate defining at least one opening; and at least one screw having a shank sized to extend through said opening and a head sized to be retained by said opening.

9. A prosthesis for the basal joint of the thumb as recited in claim 8, wherein said means for securing the first metacarpal component at the proximal end of a first metacarpal bone includes a tapered stem sized, shaped, and located to be received in a longitudinal bore in a first metacarpal bone when the securement plate abuts the outer surface of the first metacarpal bone.

10. A prosthesis for the basal joint of the thumb, comprising:
    a socket member including a socket base portion and a socket cap portion, each of said socket base portion and socket cap portion defining a partial spherical recess; and means for securing said socket base portion and socket cap portion together so that said partial spherical recesses cooperate to form an internal, partial spherical socket;
    and a first metacarpal component including means for securing the first metacarpal component at the proximal end of a first metacarpal bone and including a proximally extending, partial spherical projection, said partial spherical projection being received and supported for rotation by said partial spherical socket, with the partial spherical socket enclosing the partial spherical projection sufficiently that the partial spherical projection is retained in the partial spherical socket as long as the partial spherical projection remains intact and the socket base portion and socket cap portion are secured together and remain intact;

wherein said socket base portion has a first side shaped to conform to the side of the trapezoid bone, said socket base portion defining an internally threaded opening extending to said first side for receiving a screw to secure the socket base portion to the trapezoid.

11. A prosthesis for the basal joint of the thumb as recited in claim 10, wherein said partial spherical projection is entrapped by and cannot be dislodged from the partial spherical socket as long as the partial spherical projection remains intact and the socket base portion and socket cap portion are secured together and remain intact.

12. A prosthesis for the basal joint of the thumb, comprising:
- a socket member including a socket base portion and a socket cap portion, each of said socket base portion and socket cap portion defining a partial spherical recess; and means for securing said socket base portion and socket cap portion together so that said partial spherical recesses cooperate to form an internal, partial spherical socket;
- a first metacarpal component including means for securing the first metacarpal component at the proximal end of a first metacarpal bone and including a proximally extending, partial spherical projection, said partial spherical projection being received and supported for rotation by said partial spherical socket, with the partial spherical socket enclosing the partial spherical projection sufficiently that the partial spherical projection is retained in the partial spherical socket as long as the partial spherical projection remains intact and the socket base portion and socket cap portion are secured together and remain intact;

wherein said socket member has an external size and shape that is substantially similar to the human trapezium when the socket base and socket cap are secured together;

wherein said socket base portion has a first side shaped to conform to the side of the trapezoid bone, said socket base portion defining an internally threaded opening extending to the first side for receiving a screw to secure the socket base portion to the trapezoid;

and further comprising a screw sized to be received in said internally threaded opening, with a head of the screw retained in said internally threaded opening and a shaft of the screw projecting from the first side of the socket base a distance long enough to extend through the trapezoid bone and into the capitate bone.

\* \* \* \* \*